United States Patent [19]

Cartmell

[11] E Patent Number: Re. 32,724

[45] Reissued Date of Patent: Aug. 2, 1988

[54] REUSABLE MEDICAL ELECTRODE HAVING DISPOSABLE ELECTROLYTE CARRIER

[75] Inventor: James V. Cartmell, Dayton, Ohio

[73] Assignee: American Hospital Supply Corporation, Evanston, Ill.

[21] Appl. No.: 786,710

[22] Filed: Oct. 11, 1985

Related U.S. Patent Documents

Reissue of:

[64] Patent No.: 4,319,579
Issued: Mar. 16, 1982
Appl. No.: 215,277
Filed: Dec. 11, 1980

U.S. Applications:

[63] Continuation of Ser. No. 590,182, Mar. 16, 1984, abandoned, which is a continuation of Ser. No. 50,626, Jun. 21, 1979, abandoned.

[51] Int. Cl.[4] ..... A61B 5/04

[52] U.S. Cl. ..... 128/640; 128/803

[58] Field of Search ..... 128/639–641, 128/644, 783, 791–793, 798, 802, 803, 731

[56] References Cited

U.S. PATENT DOCUMENTS

| | | | |
|---|---|---|---|
| 3,085,577 | 4/1963 | Berman et al. | 128/641 |
| 3,279,468 | 10/1966 | LeVine | 128/792 |
| 3,498,291 | 3/1970 | Bunn | 128/644 |
| 3,565,055 | 2/1971 | Amoroso | 128/639 |
| 3,572,322 | 3/1971 | Wade | 128/640 |
| 3,580,240 | 5/1971 | Cosentino | 128/640 |
| 3,607,788 | 9/1971 | Adolph et al. | 128/640 |
| 3,746,004 | 7/1973 | Jankelson | 128/803 |
| 3,828,766 | 8/1974 | Krasnow | 128/641 |
| 3,828,766 | 8/1974 | Krasnow | 128/641 |
| 3,895,635 | 7/1975 | Justus | 128/783 X |
| 3,998,212 | 12/1976 | Anderson et al. | 128/641 |
| 4,040,412 | 8/1977 | Sato | 128/640 |
| 4,050,453 | 9/1977 | Castillo et al. | 128/640 |
| 4,051,842 | 10/1977 | Hazel et al. | 128/640 |
| 4,067,342 | 1/1978 | Burton | 128/798 |
| 4,082,086 | 4/1978 | Page et al. | 128/640 |
| 4,121,575 | 10/1978 | Mills et al. | 128/644 |
| 4,126,126 | 11/1978 | Bare et al. | 128/639 |
| 4,155,354 | 5/1979 | Rasmussen | 128/640 |

FOREIGN PATENT DOCUMENTS

| | | | |
|---|---|---|---|
| 1519782 | 8/1978 | United Kingdom | 128/640 |

*Primary Examiner*—Lee S. Cohen
*Attorney, Agent, or Firm*—Dybvig & Dybvig

[57] ABSTRACT

A medical electrode particularly suited for use as an EEG electrode comprises initially separated electrode conductor and electrolyte carrier components which are united prior to use of the electrode. The electrolyte carrier component comprises a disposable adhesive patch adhered to a disposable sponge member soaked with an electrolyte. The electrode conductor component comprises a reusable conductor ring having an affixed lead wire terminating with a plug-in device for effecting attachment to a monitoring instrument. Prior to use the electrolyte carrier components are stored in one or more evaporation resistant tray devices.

20 Claims, 1 Drawing Sheet

REUSABLE MEDICAL ELECTRODE HAVING DISPOSABLE ELECTROLYTE CARRIER

Matter enclosed in heavy brackets [ ] appears in the original patent but forms no part of this reissue specification; matter printed in italics indicates the additions made by reissue.

*This is a continuation of co-pending application Ser. No. 590,182, filed Mar. 16, 1984, now abandoned.*

This is a continuation, of application Ser. No. 050,626, filed June 21, 1979 for REUSABLE MEDICAL ELECTRODE HAVING DISPOSABLE ELECTROLYTE MEANS now abandoned.

BRIEF SUMMARY OF THE INVENTION

In the present invention, shaped initially dry absorbent bodies or sponges are adhered centrally to adhesive patches each sized to ultimately adhere an assembled electrode to the body of a subject. The sponges are then soaked with an adequate supply of electrolyte and the resulting electrolyte carrier components are placed for storage in wells of a storage tray, utilizing exposed adhesive on the adhesive patches for sealing attachment of the electrolyte carriers to the storage tray.

Electrode conductor components which are ultimately to be assembled to the aforementioned electrolyte carrier components comprise prechlorided, or otherwise suitably treated conductor ring portions, sized to surround the aforementioned electrolyte loaded sponges, said conductor ring portions having affixed lead wires which terminate distally with plug-in terminals suitable for attachment to monitoring equipment. Subsequent assembly of the electrodes is effected by sliding the electrolyte loaded sponges of the electrolyte carrier components each into a separate conductor ring portion already attached to the monitoring equipment and then applying the adhesive patches of the assembled components to the body of a subject, the dimensions of the assembled components being such that adhesive attachment to the body of the subject compresses the electrolyte loaded sponge and, as such compression occurs, securely affixes the electrolyte sponge, the conductor ring portion and the lead wire emanating from the conductor ring portion to the body of the subject.

DETAILED DESCRIPTION

Figure 1:
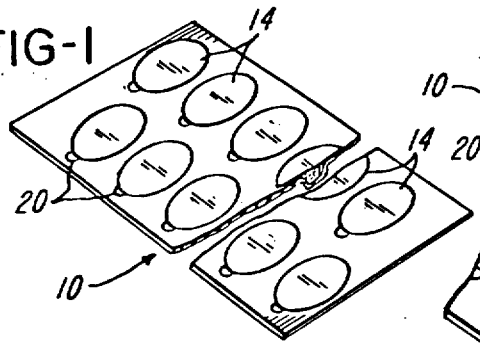
FIG. 1 is a perspective view with a portion broken away illustrating a tray supporting thereon a plurality of disposable electrolyte carrier components.
Figure 2:
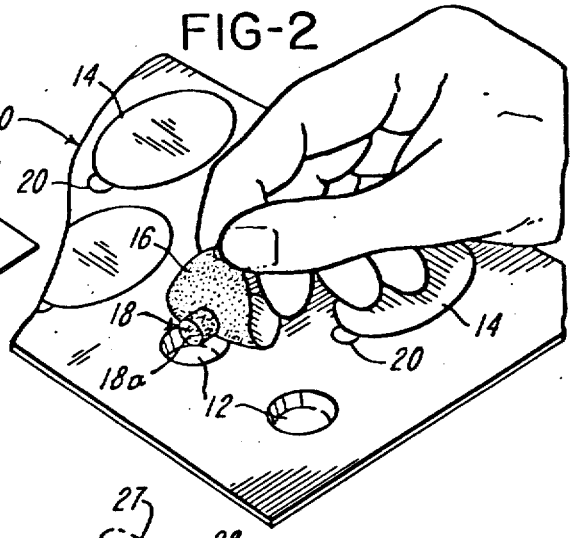
FIG. 2 is a greatly enlarged fragmentary perspective view illustrating one of the disposable electrolyte carrier components being removed from the tray.

Referring first to the disposable component of the electrode, FIGS. 1 and 2 illustrate a molded and generally planar supporting tray 10 having a plurality of recessed wells or cups 12, the wells preferably being arranged in an orderly array such as the two parallel rows illustrated in FIG. 1 with the wells in one row being offset, or staggered, with respect to the wells in the other row. Adhered to the upper surface of the tray 10 are a plurality of pliant plastic patches 14, each having an adhesive coating 16 on the side thereof which is contacted to the tray 10.

The patches 14 are preferably of an oblong or elliptical shape and each has *an electrolyte aggregate comprising* a cylindrically shaped electrolyte loaded absorbent body 18 adhered at one end thereof to a centrally disposed area of the adhesive coating 16 which otherwise surrounds the adhered absorbent body 18. The cylindrically shaped bodies are preferably adhered to the patches 14 when in a dry state productive of good adhesion and are thereafter generously soaked with a liquid electrolyte 18a.

Each of the patches 14 has a lifting tab 20 adhered to the adhesive coating 16 where it projects outside the edge margin of the patch 14 for easy finger lifting of the lifting tab 20 and therewith easy peeling of the associated patch 14 from the upper surface of the tray 10. The staggered arrangement of the wells 12 allows ample clearance between the patches 14 for finger engagement as described.

It will be noted that the electrolyte soaked bodies 18 have diameters which are small in relation to the inside diameters of the wells 12, such that when the patches 14 are peeled away from the tray 10 none of the electrolyte contained in the absorbent bodies 18 will be transferred to the walls of the wells 12. Thus the bodies 18 may be prefilled each with a measured quantity of electrolyte and since the bodies 18 are sized so as not to physically contact the tray 10, none of the measured quantity of electrolyte will be lost by transfer to the surfaces which form the wells 12.

The tray 10, which may be sized to support some 23 of the patches 14, is preferably molded or otherwise formed of a relatively moisture impermeable plastic, such as polyethylene. The patches 14 are preferably formed of a relatively limp moisture impervious plastic, such as a vinyl plastic. The adhesive comprising the adhesive surface 16 is preferably a pressure sensitive medical adhesive of which a number of types are commercially available.

With the adhesive surfaces 16 securely affixing the patches 14 of the upper surface of the tray 10, the wells 12 are sealed against the entry of ambient atmosphere and the electrolyte soaked bodies or sponges 18 protected against evaporation of the electrolyte for long periods of time.

The formed absorbent bodies 18 are conveniently punched out of a sheet of a foamed plastic, such as a polyurethane plastic of the open cell type. However, other absorbent bodies, such as fibrous gauzes, sponges and the like may be utilized in lieu of foamed plastics.

Figure 4:
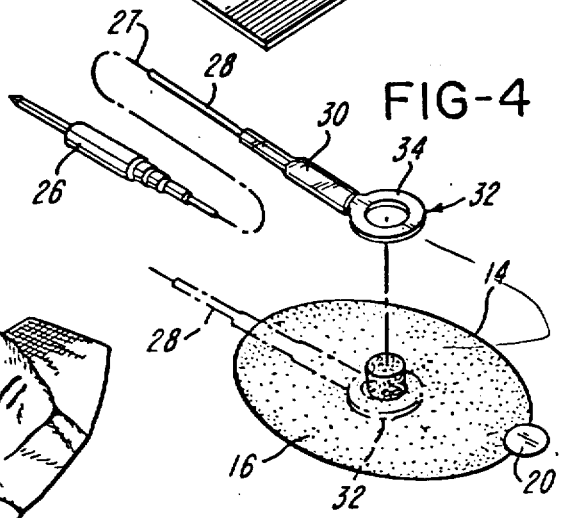
FIG. 4 is a greatly enlarged fragmentary perspective view illustrating the reusable electrode component in solid lines before assembly to the disposable component and in broken lines after assembly to the disposable component.

The reusable portion of the electrode, which is best illustrated in FIG. 4, comprises a stamped metal terminal 32 for transmitting electrical signal of the type comprising a circular ring 34 having a radially disposed integrally formed lug extending outwardly from the ring. The outwardly extending terminal lug does not fully appear in the drawings because covered by a shrink-fitted plastic sleeve 30. Before being covered by the sleeve 30 the lug is attached by solder, or the like, not shown, to an electrical conductor 27 covered by an insulating sheath so as to form an insulated wire 28. It can be noted that the sleeve 30 is of such a length that approximately one-half of the sleeve covers the lug emanating from the terminal 32 and the remainder of the sleeve snugly surrounds the wire 28. As those skilled in the art will appreciate, the solder connection between the conductor 27 and the terminal lug may be overpainted with a moisture impervious plastic, not shown, so as to assure that no electrolyte from the body 18 will have access to the solder or to the conductor 27.

The terminal 32 is preferably a very high quality silver, such as 99.9% silver, and the terminal lug extending through the sleeve 30, being one piece with the terminal ring 34, would of course comprise the same high quality silver. The outer surfaces of the terminal ring 34 are preferably chlorided by contacting the ring 34 with any suitable chloriding solution. This chloridization preferably occurs before the sleeve 30 is shrunk into position so as to assure that no part of the terminal ring 34, which is later permitted to contact electrolyte as will be explained, has not been first chlorided. The sleeve 30 is preferably any moisture impervious heat shrinkable plastic, such as tetrafluoroethylene (Teflon).

The end of the conductor 27 which has been soldered to the terminal lug covered by the sleeve 30 may be referred to as the proximal end of the wire 28. The opposite or distal end of the wire 28 is soldered, or otherwise connected, to a conventional bayonet plug 26 which, as will be described, is used for connecting the assembled electrode to an external signal monitoring device, such as an electroencephalograph recording device.

As apparent in FIG. 4, the disposable and the reusable electrode components are assembled together by passing the chlorided ring 34 over any one of the electrolyte soaked bodies 18, such bodies having been sized with a diameter only slightly less than the inside diameter of the ring 34. FIG. 4 illustrates the ring 34 and associated wire 28 before assembly to the disposable component in solid lines and shows by broken lines the manner in which the ring 34 fits over the electrolyte soaked body 18 so as to become adhered to the adhesive layer 16 present on the patch 14 and surrounding the body 18.

Figure 3:
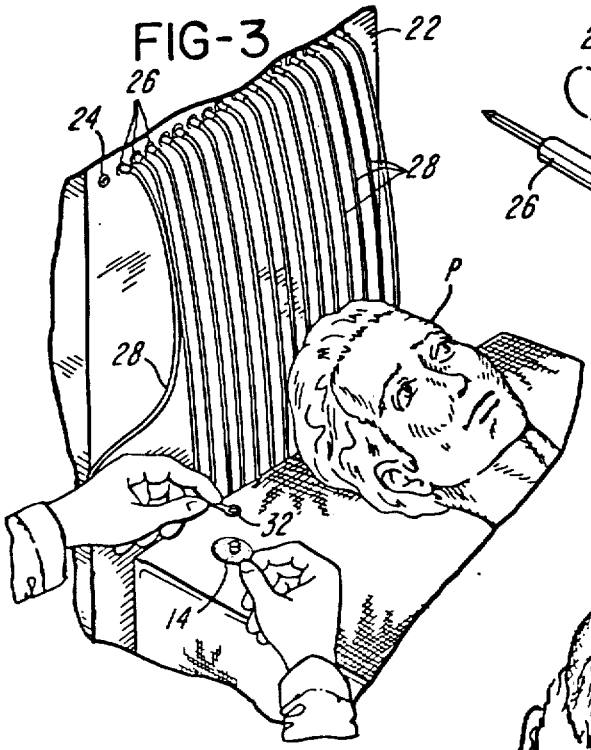
FIG. 3 is a fragmentary perspective view schematically illustrating the manner in which a disposable electrolyte carrier component is attached to a reusable electrode component in preparation for affixation of an assembled electrode to a subject.

FIG. 3 illustrates a patient P lying adjacent an EEG terminal board 22 in preparation for an EEG examination. The terminal board 22 is provided with a number of bayonet receptacles 24. Plugged into a number of the receptacles 24 are bayonet plugs 26 from which dangle insulated wires 28. The insulated wires may be, for example, 4 ft. in length.

EEG examinations typically involve the mounting of a large number of recording electrodes to the scalp and sometimes other parts of the body of the patient and the simultaneous recording of a plurality of traces derived from combinations of the mounted electrodes. Individual traces, each of which may be derived from a combination of two or more electrodes, are simultaneously recorded side-by-side on an EEG chart. Any one of the side-by-side traces is sometimes referred to as a channel and a display of a plurality of side-by-side traces or channels is typically referred to as a montage.

Each single recording of a trace or channel involves a comparison of electrodes attached to different portions of the patient's scalp or body, with the resultant trace being the difference in the voltages derived from the patient's body by means of the electrodes. A trace produced by a large number of electrodes all referenced to a single other electrode is sometimes referred to as a monopolar trace or channel. A trace in which one electrode is referenced to a single other electrode is typically referred to as a bipolar trace or channel.

The number and location of the wires 28 and receptacles 24 employed during any monitoring procedure varies depending upon the number of traces or channels forming the montage desired to be accomplished. As a convenience, wires 28 may be color coded or otherwise marked to simplify wire selection for montage formation.

Figure 5:
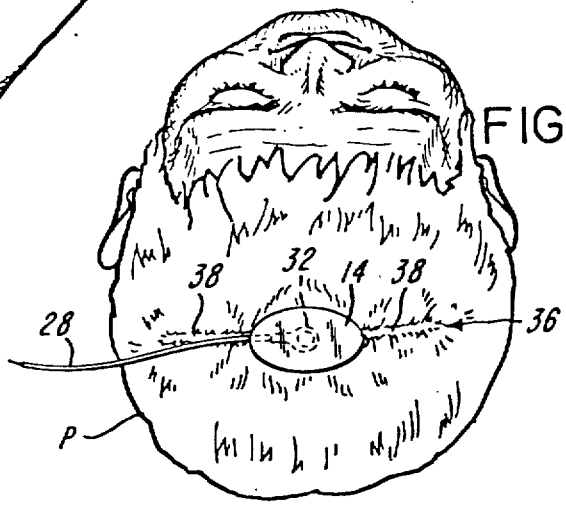
FIG. 5 is a fragmentary perspective illustration of an assembled electrode applied to the unshaven scalp of a subject.

As appears in FIG. 3 an attendant has selected a given one of the wires 28 for passage of its terminal ring portion 34 onto an electrolyte soaked body 18 protruding from an adhesive patch 14. Then, as shown in FIG. 5, the assembled electrode is applied to the patient's scalp after separating the patient's hair so as to form a part 36 which exposes a portion of the patient's skin surface 38. The direction in which the part 36 extends will obviously depend on the direction in which the patient's hair has been parted and the location of the electrode along such part in turn depends upon the nature of the montage sought to be produced.

In general, the illustrated elliptical shape for the patches 14 is preferred. Thus the direction in which a particular part of the patient's hair extends is subject to the control of the attendant who can so arrange the hair partings that the major axes of the elliptical patches extend along the hair partings so as to maximize adhesive contact with the skin exposed by such partings without, at the same time, generating unmanageable overlaps between patches required to be mounted in close proximity.

As apparent in FIG. 5 it is also desirable that the wire 28 also extend along the part 36 so that a minimum of the patient's hair lies under the wire 28, with the consequence that the wire position is firmly anchored and tensions developed along the length of the wires will have a minimal affect upon the electrode position.

It can be appreciated that as the patch 14 is pressed against the patient's scalp, the electrolyte loaded body 18 will be compressed in that the body 18 is longer than the ring portion 34 is thick. This compression generously wets with electrolyte the patient's scalp under the patch 14 and, at the same time, expands the body 18 against the inside wall of the ring 34 so as to effect a secure attachment between the body 18 and the ring 34. Inasmuch as the rings 34 will have been prechlorided, or otherwise treated, it can be appreciated that assembled electrodes are ready immediately for signal monitoring.

In the foregoing description, the patches 14 with their accompanying electrolyte loaded bodies 18 have been characterized as disposable electrolyte components, or carriers. Thus upon completion of the monitoring desired to be accomplished, the patches 14 may be readily removed from the patient's scalp with the aid of a solvent in conventional fashion and then the patches 14, together with the electrolyte loaded bodies 18, discarded. The lead wire 28 together with the prechlorided terminal ring 34 may then be cleaned under suitably aseptic conditions and reused with a clean and previously unused disposable electrolyte carrier. The number of times the reusable electrode part may be reused will, of course, depend upon the permanency of the chloriding process or other electrode preparation procedure and the abrasiveness of the aseptic cleaning process used between successive monitoring operations. Those skilled in the art will appreciate, of course, that chloriding is frequently the most desirable preparation for an electrode metal such as silver which is relatively noble and that when lesser electrode metals, such as tin or copper, are to be employed in the practice of the present invention, chloriding may be less desirable.

Although the preferred embodiment of this invention has been described, it will be understood that various changes may be made within the scope of the appended claims. *As used herein, the term "aggregate" means an assemblage or group of distinct particulars massed together.*

Having thus described my invention, I claim:

1. A medical electrode comprising a disposable portion and a reusable portion, said disposable portion comprising a shaped absorbent body soaked with an electrolyte and a pliant sheet member having an adhesive layer on one side thereof, said adhesive layer adhering an end of said body to said one side of said sheet member, said body protruding outwardly from said adhesive layer, said reusable portion comprising terminal means for transmitting electrical signals and readily separable from said disposable portion, said terminal means having an inside wall embracing and substantially surrounding said shaped body.

2. The medical electrode of claim 1 wherein said shaped body is a cylindrical body and said end adhered to said adhesive layer is disposed at one end of said cylindrical body.

3. The medical electrode of claim 2 wherein said terminal means uninterruptedly surrounds said cylindrical body.

4. The medical electrode of claim 3 wherein said terminal means comprises a ring portion having an outward projection from said adhesive layer of said sheet member which is less than the outward protrusion of said shaped body from such adhesive layer.

5. The medical electrode of claim 1 wherein said sheet member is an oblong sheet member.

6. The medical electrode of claim 5 wherein said oblong sheet member is elliptically shaped.

7. The medical electrode of claim 1 wherein said sheet member is a vinyl plastic sheet member.

8. The medical electrode of claim 1 wherein said inside wall is a metal wall.

9. The medical electrode of claim 8 wherein said metal wall is silver metal.

10. The medical electrode of claim 8 wherein the metal of said wall is chloridized.

11. The medical electrode of claim 1 wherein said sheet member has an edge margin surrounding said protruding body and spaced from said protruding body.

12. The medical electrode of claim 11 wherein a portion of said adhesive layer disposed between said shaped body and said edge margin adheres to a portion of said terminal means.

13. The medical electrode of claims 1, 2, 3, 4, 5, 6, 7, 8, 9, 10, 11 or 12 wherein said sheet member is moisture impervious.

14. The medical electrode of claim 13 wherein said sheet member is imperforate.

15. In the method of preparing a patient for monitoring electrical signals available at the body of the patient the steps comprising connecting a distal end portion of a lead wire to a monitoring instrument, connecting a proximal end portion of said lead wire to electrode terminal means for transmitting electrical signals, adhesively attaching a shaped absorbent body to an adhesive coating on a patch member, soaking said shaped body with an electrolyte, inserting said electrolyte soaked body in said electrode terminal means, and placing said soaked body in contact with the body of the patient by adhesively affixing the adhesive coating on said patch member over said terminal means to the patient.

16. The method of claim 15 wherein the placement of said soaked body in contact with the body of the patient comprises the additional steps of parting the hair of the patient, positioning a portion of the lead wire connected to said electrode terminal means along the part formed by parting the patient's hair, and pressing said adhesive patch member over said lead wire and onto the patient's hair to secure said electrolyte soaked body and said electrode terminal means to the body of the patient.

*17. In combination:*

*a one-piece, imperforate and moisture impervious pliant plastic sheet;*

*an adhesive layer completely coating one side of said sheet;*

*an aggregate comprising an electrolyte and a shaped body for containing said electrolyte, said body having a planar end surface facing toward said sheet and said body being adhered to a part of said adhesive layer which is spaced from the margin of said sheet by engagement of the entirety of said planar surface with said part; and*

*relatively moisture impevious means providing a support having a supporting surface, said supporting surface being adhesively engaged to peripheral portions of said adhesive layer surrounding said part,*

*said sheet and said adhesive layer thereby cooperating with said support-providing means to seal said aggregate from the atmosphere surrounding said support-providing means.*

*18. In a medical electrode of the type comprising a disposable portion and a reusable portion;*

*the improvement wherein said reusable portion comprises metal terminal means connected to an insulated lead means for attachment to peripheral equipment; and*

*said disposable portion comprises:*

*a. a one-piece, imperforate and moisture impervious pliant plastic sheet;*

*b. an adhesive layer completely coating one side of said sheet; and*

*c. an aggregate comprising an electrolyte and a shaped body for containing said electrolyte, said body having a planar end surface facing toward said sheet and said body being adhered to a part of said adhesive layer which is spaced from the margin of said sheet by engagement of the entirety of said planar surface with said part;*

*said reusable portion being so constructed that said terminal means may be located between said adhesive layer and the skin of a patient in engagement with said aggregate with a portion of said lead means located between said adhesive layer and the skin of the patient.*

*19. Apparatus for assembling a medical electrode on the skin of a patient comprising:*

*A. means providing a relatively moisture impervious support having a supporting surface;*

*B. a disposable assembly removably supported by said means providing a support comprising:*

*a. a one-piece, imperforate and moisture impervious pliant plastic sheet;*

*b. an adhesive layer completely coating one side on said sheet;*

*c. means forming a shaped body adhered to a part of said adhesive layer separated from the margin thereof for containing an electrolyte, peripheral portions of said adhesive layer surrounding said electrolyte containing means being engaged with said supporting surface so that said sheet and said adhesive layer cooperate with said support providing means to seal said electrolyte containing means from the atmosphere surrounding said support providing means; and*

*C. a reusable portion comprising an insulated lead wire having a metallic terminal which is uninsulated so that said disposable assembly may be removed from said support providing means and placed over the skin of a patient with said terminal covered by said sheet and also engaging said electrolyte containing means to form an electrode held to the skin of a patient by said adhesive layer.*

*20. A method of assembling a medical electrode onto the skin of a patient comprising the steps of:*

*providing a disposable assembly comprising means forming an imperforate pliant sheet of moisture impervious plastic having an adhesive layer completely coating one side thereof and further comprising means forming a shaped body adhered to a part of said adhesive layer separated from the margin thereof for containing an electrolyte;*

*mounting said disposable assembly onto means providing a relatively moisture impervious support with said disposable assembly removably attached to said support providing means by a marginal portion of said adhesive layer surrounding said part of said adhesive layer;*

*removing said disposable assembly from said support providing means when the medical electrode is to be assembled onto the skin of a patient; and*

*adhering said disposable assembly in contact with the skin of the patient by engaging said marginal portion of said adhesive layer to the skin with an uninsulated terminal of an insulated layer wire engaging said electrolyte containing means and held between said sheet forming means and the patient's skin.*

* * * * *

UNITED STATES PATENT AND TRADEMARK OFFICE

CERTIFICATE OF CORRECTION

PATENT NO. : RE 32,724

DATED : August 2, 1988

INVENTOR(S) : James V. Cartmell

It is certified that error appears in the above-identified patent and that said Letters Patent is hereby corrected as shown below:

Claim 20, line 22, "layer" should be --lead--.

Signed and Sealed this

Twenty-eighth Day of August, 1990

*Attest:*

HARRY F. MANBECK, JR.

*Attesting Officer*

*Commissioner of Patents and Trademarks*